(12) United States Patent
Krill et al.

(10) Patent No.: US 10,766,847 B2
(45) Date of Patent: *Sep. 8, 2020

(54) METHOD FOR PRODUCING METHYLMETHACRYLATE

(71) Applicant: RÖHM GMBH, Darmstadt (DE)

(72) Inventors: Steffen Krill, Muehtal (DE); Torsten Balduf, Pfungstadt (DE); Martin Koestner, Darmstadt (DE); Matthias Groemping, Darmstadt (DE); Alexander Lygin, Griesheim (DE); Rudolf Burghardt, Darmstadt (DE)

(73) Assignee: RÖHM GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/161,395

(22) Filed: Oct. 16, 2018

(65) Prior Publication Data

US 2019/0112255 A1    Apr. 18, 2019

Related U.S. Application Data

(63) Continuation of application No. 15/795,887, filed on Oct. 27, 2017, now Pat. No. 10,273,201, which is a continuation of application No. 14/784,320, filed as application No. PCT/EP2014/057380 on Apr. 11, 2014, now Pat. No. 9,890,105.

(30) Foreign Application Priority Data

Apr. 19, 2013 (EP) .................... 13002076

(51) Int. Cl.
  *C07C 45/75* (2006.01)
  *C07C 67/39* (2006.01)

(52) U.S. Cl.
  CPC .............. *C07C 67/39* (2013.01); *C07C 45/75* (2013.01)

(58) Field of Classification Search
  None
  See application file for complete search history.

(56) References Cited

U.S. PATENT DOCUMENTS

| 2,848,499 A | 8/1958 | MacLean et al. |
| 4,283,564 A | 8/1981 | Bernhagen et al. |
| 4,496,770 A | 1/1985 | Duembgen et al. |
| 5,969,178 A | 10/1999 | Okamoto et al. |

FOREIGN PATENT DOCUMENTS

| CN | 101074192 A | 11/2007 |
| DE | 28 55 504 | 6/1980 |
| EP | 0 092 097 | 10/1983 |
| EP | 0 890 569 | 1/1999 |
| WO | WO 98/11050 A1 | 3/1998 |

OTHER PUBLICATIONS

International Search Report dated May 26, 2014 in PCT/EP14/057380 Filed Apr. 11, 2014.
European Search Report dated Jul. 19, 2013 in Application No. EP 13002076.1 Filed Apr. 19, 2013.
Dimitratos, et al. Chem. Sci., 2012, 3, 20-44.
Written Opinion dated May 17, 2016 in Singaporean Patent Application No. 11201508639W.
James M. Church, et al. "Methyl Methacrylate from methallyl alcohol", Industrial and Engineering Chemistry, vol. 42, No. 5, 1950, pp. 768-776.

*Primary Examiner* — Ana Z Muresan
(74) *Attorney, Agent, or Firm* — Oblon, McClelland, Maier & Neustadt, L.L.P.

(57) ABSTRACT

The present invention relates to a process for producing methyl methacrylate, comprising the following steps: A) producing methacrolein and B) reacting the methacrolein obtained in step A) in an oxidative esterification reaction to give methyl methacrylate, characterized in that the two steps A) and B) take place in a liquid phase at a pressure of from 2 to 100 bar, and step B) is carried out in the presence of a heterogeneous noble-metal-containing catalyst comprising metals and/or comprising metal oxides.

19 Claims, 3 Drawing Sheets

METHOD FOR PRODUCING METHYLMETHACRYLATE

CROSS-REFERENCE TO RELATED APPLICATIONS

This application is a continuation application of Ser. No. 15/795,887, filed Oct. 27, 2017, which is a continuation application of Ser. No. 14/784,320, now granted as U.S. Pat. No. 9,890,105, filed Oct. 14, 2015 which is a National stage entry of PCT/EP2014/057380 filed Apr. 11, 2014, which claims priority to European Patent Application No. 13002076.1 filed Apr. 19, 2013. The contents of these applications are incorporated herein by reference in their entirety.

The present invention relates to a process for producing methyl methacrylate by direct oxidative esterification of methacrolein and the production of methacrolein.

Large quantities of methyl methacrylate are used for producing polymers and copolymers with other polymerizable compounds. Methyl methacrylate is moreover an important building block for various speciality esters of methacrylic acid (MAA), these being produced by transesterification with the corresponding alcohol.

It is therefore highly desirable that the said starting material can be produced by a process which is as simple as possible, and cost-effective and protects the environment.

Methyl methacrylate (MMA) is nowadays mostly produced from hydrogen cyanide and acetone by way of the resultant acetone cyanohydrin (ACH) as main intermediate. This process has the disadvantage of producing very large amounts of ammonium sulphate, treatment of which incurs very high costs. Other processes not based on ACH are described in the relevant patent literature and are also carried out on a production scale. Among the raw materials used in this context as starting materials are those based on C-4 compounds, for example isobutylene or tert-butanol, which are converted by way of a plurality of stages to the desired methacrylic acid derivatives.

The general procedure here is that isobutylene or tert-butanol is oxidized in a first stage to give methacrolein, which is then reacted with oxygen to give methacrylic acid. Methanol is then used to convert the resultant methacrylic acid to MMA. Further details of the said process are described inter alia in Ullmann's Encyclopedia of Industrial Chemistry 2012, Wiley-VCH Verlag GmbH & Co. KGaA, Weinheim, Methacrylic Acid and Derivatives, DOI: 10.1002/14356007.a16_441. pub2, and in Trends and Future of Monomer-MMA Technologies, SUMITOMO KAGAKU 2004-II.

Ethylene can also be used as starting material instead of a $C_4$ building block such as isobutylene in one variant of said production method, and is first reacted with synthesis gas to give propanal; reaction with formaldehyde then gives methacrolein. The resultant methacrolein is oxidized by air in the gas phase on a heterogeneous catalyst to give methacrylic acid, which is esterified with methanol to give MMA (Ullmann's Encyclopedia of Industrial Chemistry 2012, Methacrylic Acid from Ethylene, and Trends and Future of Monomer-MMA Technologies, SUMITOMO KAGAKU 2004-II). This process has been operated since 1990 by BASF in a plant with a capacity of 40 000 metric tons per annum for methacrylic acid production. According to the SUMITOMO article, this process was developed by BASF for specific requirements, and it is therefore difficult to make general use of said process for producing larger quantities of MMA.

Another process obtains MMA through oxidation of isobutylene or tert-butanol with atmospheric oxygen in the gas phase on a heterogeneous catalyst to give methacrolein followed by use of methanol in an oxidative esterification reaction of methacrolein. This process, developed by ASAHI, is described inter alia in the publications U.S. Pat. Nos. 5,969,178 and 7,012,039. This process is also described in the SUMITOMO article, which provides detailed information about the disadvantages of said process, consisting in particular in high energy usage, arising inter alia because of an unpressurized procedure.

In addition, other problems associated with all the processes described above are in particular the relatively unsatisfactory yield, high losses in the oxidation steps and attendant $CO_2$ formation, and in general terms the attendant formation of by-products requiring complicated steps to isolate the product: all of the processes starting from isobutylene or from equivalent C-4-based raw materials, such as TBA or MTBE, using gas-phase oxidation on a heterogeneous catalyst system achieve yields below 90%, and the relevant literature describes yields below 85% for methacrolein production starting from isobutylene (e.g. Table 5 in Ullmann's Encyclopedia/Sumitomo, see above). The gas-phase process naturally proceeds at moderate pressures of from 1 to 2 bar absolute, and produces a process gas which comprises only about 4-6% by volume of the product component. Isolation of the useful product from the inert gas ballast incurs accordingly high energy cost and consumes large amounts of cooling energy, as well as steam for multi-stage distillative work-up steps.

Production of MMA according to the methods described hitherto produces relatively large amounts of wastes, in particular exhaust gases or wastewater, which require expensive disposal.

Conduct of some of the processes described above moreover requires very complex, and therefore expensive, plant, with associated high capital expenditure and high maintenance costs.

The overview article cited above from SUMITOMO describes the respective disadvantages in detail, and can therefore be incorporated herein by way of reference.

Furthermore, Patent Application CN 101074192 describes an MMA production process in which methacrolein is first prepared from propanal and formaldehyde at a temperature in the range from 40 to 45° C. and with a reaction time in the range from 30 to 100 minutes, and is then oxidized with methanol to give MMA. In addition, a similar process is proposed by Yuchao Li et al. "*Synthesis of methacrolein by condensation of propionaldehyde with formaldehyde*", Advance Materials Research Vols. 396-398 (2012). pp. 1094-1097. Said publication expressly advises avoidance of operation at elevated temperature or at superatmospheric pressure. Said process has the disadvantage of a high requirement on acid and amine, these being used to catalyse the reaction. Consequently large amounts of waste products are produced, since a substantial proportion of the amine is destroyed under the conditions mentioned. One of the side reactions, which deactivates the catalyst, is the Eschweiler-Clarke reaction which leads to formation of methylated tertiary amine which is then not capable of catalysing the Mannich reaction (U.S. Pat. No. 4,408,079, column 2, lines 15 ff): by way of example, dimethylamine becomes trimethylamine.

If, as described by Li, operations are then carried out at or in the vicinity of atmospheric pressure with large stoichiometric amounts of catalyst base, increased deactivation of the catalyst occurs, and the resultant procedure is therefore not cost-effective. These problems incur high costs which make the process described relatively uneconomic. The long reaction time resulting from unpressurized conduct of the reaction is another serious disadvantage of both of these processes.

EP 0 890 569 discloses a process for the production of methyl methacrylate by direct oxidative esterification of methacrolein with methanol. EP 0 890 569 explicitly teaches here that a low water content of less than 2% by weight, preferably less than 1% by weight, in the methacrolein is essential for the oxidative esterification. The examples list exclusively reactions with water content below 0.8% by weight. Furthermore, according to this teaching it is important that the total content of contaminants must be small. EP 0 890 069 therefore teaches oxidative production of methacrolein in the gas phase from isobutylene with oxygen, and then complicated dewatering of the methacrolein in a column.

Although EP 0 092 097 and DE 28 55 504 teach an alternative synthesis process for methacrolein in the liquid phase, in a process where propanal is reacted with formaldehyde, this process produces a large amount of water which according to the teaching of EP 0 890 569 renders this type of process unsuitable without complicated purification as precursor stage for the oxidative esterification of methacrolein to methyl methacrylate. The starting materials and by-products used in this process, for example dimeric methacrolein, also potentially exert a yield-reducing or detrimental effect in oxidative esterification, alongside the high water content: the product according to DE 28 55 504 comprises more than 5% by weight of an aldol by-product which would be detrimental in oxidative esterification and would inevitably require complicated purification of the methacrolein.

In the light of the prior art, an object of the present invention is therefore to provide a technically improved MMA production process which does not have the disadvantages of conventional processes.

A particular objective is to enable the production of MMA with a relatively low energy usage. Furthermore the process shall be carried out in a manner that provides a high level of protection of the environment, so that the quantities of wastes obtained are very small. A particular object of the present invention is to improve the overall yield of MMA, based on the raw materials used, for example by discovering and combining individual reaction steps with high product selectivity.

Moreover, it should be possible to carry out the process with a very small number of steps, which should be simple and reproducible.

In addition, it should be possible to carry out the process by using relatively simple and inexpensive plant. Capital expenditure for the plant should accordingly be small. Maintenance of this plant should be simple and inexpensive.

Other objects not explicitly mentioned are apparent from the overall context of the description and claims hereinafter.

A process with all of the features of patent claim 1 achieves the above objects, and also achieves other objects which are not explicitly mentioned, but which are readily derivable or deducible from the circumstances discussed in the introduction of this specification. Dependent claims 2 to 18 protect advantageous embodiments of the claimed MMA production process.

Accordingly, the present invention provides a process for producing MMA, comprising the following steps:

A) producing methacrolein from propanal and formaldehyde and
B) reacting the methacrolein obtained in step A) in an oxidative esterification reaction to give MMA, which is characterized in that the two steps A) and B) take place in a liquid phase at a pressure of from 2 to 100 bar, and step B) is carried out in the presence of a heterogeneous noble-metal-containing catalyst comprising metals and/or comprising metal oxides.

By virtue of the claimed process it is possible, in a manner that was not foreseeable, to provide an MMA production process which does not have the disadvantages of conventional processes. Surprisingly, it has been found here that, contrary to the general teaching of the prior art, steps A) and B) can also be combined without any complicated intervening purification or dewatering of the methacrolein, and lead to high methyl methacrylate yields.

In particular, MMA can be produced with relatively low energy usage. The process can moreover be carried out in a manner that provides a high level of protection of the environment, giving relatively small quantities of wastes and substantially increasing atom efficiency.

In particular, neither of the reaction steps A) and B) in the claimed process requires that additional water be introduced into the reaction mixture and then in turn removed, and overall reaction volumes and volume flow rates can therefore be kept low.

The process can moreover be carried out with relatively few steps, and these are simple and reproducible and proceed with relatively high space-time yields.

Catalyst requirement, in particular organic base requirement per metric ton of MMA produced, is moreover very small.

The process can moreover be carried out with relatively simple and inexpensive plant. Capital expenditure for the plant is low. Maintenance of this plant is simple and inexpensive.

In this context it should be stated that, in comparison with the processes according to the prior art, the number of return streams and the magnitude of these have been reduced.

The by-products produced can moreover be removed very simply from the reaction mixtures, and the overall process can therefore be carried out with high yield, without any need for complicated purification steps.

Step A)

The claimed process comprises the production of methacrolein. The processes suitable for this purpose are known to the person skilled in the art and are subject matter of relevant overview articles, for example in Ullmann's Encyclopedia of Industrial Chemistry 2012, Wiley-VCH Verlag GmbH & Co. KGaA, Weinheim, Acrolein and Methacrolein, DOI: 10.1002/14356007.a01_149. pub2.

The first stage of the process of the invention comprises the reaction of propanal with formalin to give methacrolein.

Particularly suitable processes are those in which the total amount of separately added water or, respectively, water vapour during the conduct of the process is not greater than 100 mol %, preferably 50 mol %, particularly preferably 30 mol %, and most preferably 10 mol %, based in each case on methacrolein. The most suitable processes for producing methacrolein are those where there is no reaction step in which water is added separately to the reaction mixture. The water introduced with the reactants and/or catalysts, as well as the produced water of reaction are here excluded.

Surprisingly, however, the water content is not very relevant, or at concentrations of up to 5% by weight has almost no adverse effect on the oxidative esterification of step B). In the light of the cited prior art it is therefore in particular surprising that methacrolein synthesis from propanal and formaldehyde can be combined with oxidative esterification, and indeed that it is optionally possible to omit any dewatering after step A).

The reaction, which is achieved by way of an aldol condensation or Mannich condensation, is not per se critical. However, preferred processes are those which feature high yield and low by-product formation.

It is therefore preferable to use reactions which have a selectivity of at least 80%, preferably at least 90% and particularly preferably at least 92%, based on the amount of propanal used.

Moreover, preference is given to reactions which have a high yield and high conversions by a single passage through the reaction zone. Preferred reactions feature a yield and conversions of at least 80%, preferably at least 90% and particularly preferably at least 92%, based on the amount of propanal used.

It can also be provided that the reaction according to step A) takes place with a molar ratio of propanal to formaldehyde which is preferably in the range from 2:1 to 1:2, particularly preferably from 1.5:1 to 1:1.5 and specifically preferably from 1.1:1 to 1:1.1. It is very particularly preferable to use an equimolar ratio of propanal to formaldehyde. It is thus possible, in particular at high conversions, to omit any removal and return of propanal and/or formaldehyde from the mixture obtained after the reaction according to step A).

The reaction of propanal with formaldehyde generally uses catalysts, and various systems are known here which lead to a high yield of methacrolein, with high selectivity.

Preferred processes for producing methacrolein starting from propanal and formaldehyde are described inter alia in the publications U.S. Pat. No. 7,141,702; DE 32 13 681 A1; U.S. Pat. Nos. 4,408,079; 2,848,499; JP 4173757A (JP 19900300135); JP 306942062 and EP 0 317 909 A2, and for purposes related to disclosure the teaching of the said publications is hereby incorporated by way of reference into the present application.

The reaction of propanal with formaldehyde is carried out in the presence of acid, generally inorganic acid or organic mono-, di- or polycarboxylic acid, preferably monocarboxylic acid, in particular aliphatic monocarboxylic acid.

Carboxylic acids advantageously used are aliphatic monocarboxylic acids having from 1 to 10, preferably from 2 to 4, carbon atoms, or di- and polycarboxylic acids having from 2 to 10, preferably 2 and from 4 to 6, carbon atoms. The dicarboxylic acids and polycarboxylic acids can be aromatic, araliphatic, and preferably aliphatic, carboxylic acids. Suitable examples are acetic acid, propionic acid, methoxyacetic acid, n-butyric acid, isobutyric acid, oxalic acid, succinic acid, tartaric acid, glutaric acid, adipic acid, maleic acid, and fumaric acid. In principle, it is equally possible to use other organic acids, but they are generally less advantageous for reasons of price. Inorganic acids used are generally sulphuric acid and phosphoric acid. Acid mixtures can also be used.

It is particularly preferable to use at least one organic acid for the reaction of propanal and formaldehyde, and even more preferably acetic acid.

The proportion of acid, based on propanal, is from 0.1 to 20 mol %, advantageously from 0.5 to 10 mol %, preferably from 1 to 5 mol %.

The reaction of propanal with formaldehyde is carried out in the presence of organic bases, preferably amines, particularly preferably secondary amines. Amines that can be used are preferably those of the formula $R^1R^2NH$, where $R^1$ and $R^2$ are identical or different and are respectively an alkyl moiety having from 1 to 10, advantageously from 1 to 8, in particular from 1 to 4, carbon atoms, which can also have substitution by ether, hydroxy, or secondary or tertiary amino groups, in particular by from 1 to 2 of said groups, or are an aralkyl moiety having from 7 to 12 carbon atoms or a cycloalkyl moiety having from 5 to 7 carbon atoms, and $R^1$ and $R^2$ can also, with the adjacent nitrogen, be members of a heterocyclic, advantageously 5- to 7-membered ring which can also comprise another nitrogen atom and/or an oxygen atom and which can have substitution by hydroxyalkyl or alkyl groups having from 1 to 4 carbon atoms.

Examples of amines that can be used are: dimethylamine, diethylamine, methylethylamine, methylpropylamine, dipropylamine, dibutylamine, diisopropylamine, diisobutylamine, methylisopropylamine, methylisobutylamine, methyl-sec-butylamine, methyl(2-methylpentyl)amine, methyl(2-ethylhexyl)amine, pyrrolidine, piperidine, morpholine, N-methylpiperazine, N-hydroxyethylpiperazine, piperazine, hexamethyleneimine, diethanolamine, methylethanolamine, methylcyclohexylamine, methylcyclopentylamine, dicyclohexylamine or appropriate mixtures.

It may also be provided that at least one of the amines used has no hydroxy group. It is particularly preferable that the proportion of amines having at least one hydroxy group is at most 50% by weight, preferably at most 30% by weight, and particularly preferably at most 10% by weight, based on the weight of the amines used.

The proportion of organic base, preferably of secondary amines, is from 0.1 to 20 mol %, advantageously from 0.5 to 10 mol %, preferably from 1 to 5 mol %, based on propanal.

The ratio of the equivalents of amine to acid is preferably selected in such a way as to give a resultant pH of from 2.5 to 9 in the reaction mixture prior to the reaction.

It can also be provided that the molar ratio of acid to organic base, preferably amine, is in the range from 20:1 to 1:20, preferably in the range from 10:1 to 1:10, particularly preferably in the range from 5:1 to 1:5 and specifically preferably in the range from 2:1 to 1:2.

The reaction temperature for the reaction of propanal with formaldehyde at the exit from the reaction zone is from 100 to 300° C., preferably from 130 to 250° C., with preference from 140 to 220° C., in particular from 150 to 210° C.

The reaction pressure is in the range from 2 to 300 bar, preferably from 5 to 250 bar, particularly preferably from 10 to 200 bar, advantageously from 15 to 150 bar, preferably from 20 to 100 bar and in particular from 40 to 80 bar. Pressure and temperature are adjusted in such a way that the reaction always takes place below the boiling point of the reaction mixture, i.e. the reaction proceeds in the liquid phase.

For the purposes of the present application, all pressure data are absolute pressure in the unit bar.

The residence time or reaction time is preferably at most 25 minutes, advantageously from 0.01 to 25 minutes, more advantageously from 0.015 to 10 minutes, preferably from 0.03 to 2 minutes. The residence time or reaction time is particularly preferably in the range from 0.1 to 300 seconds, specifically preferably in the range from 1 to 30 seconds. It is advantageous to use a tubular reactor as reactor at residence times below 10 minutes. The residence time here refers to the time for which the reaction mixture is reacted. All of the components are present here at reaction pressure and temperature, and the said time can therefore be calculated from the distance between the mixing point and the depressurization point. The depressurization point is the point at which the mixture is brought from reaction pressure to a pressure below 5 bar.

The reaction mixtures can also comprise, alongside water, organic solvents, e.g. propanol, dioxane, tetrahydrofuran, and methoxyethanol.

It can also be provided that the reaction of propanal with formaldehyde to give methacrolein according to step A) takes place in the presence of preferably at least 0.1% by weight, with preference at least 0.2% by weight and particularly preferably at least 0.5% by weight, of methanol, based on formalin. Despite the said relatively high methanol concentrations, by virtue of the claimed conduct of the reaction for the subsequent step B) it is possible to omit any complicated removal of methanol at the stage of formalin production and/or of methacrolein purification.

According to one particular embodiment, formaldehyde and propanal can be mixed before the said starting materials are brought to reaction pressure and/or temperature.

The reaction can be carried out as follows: a mixture of propanal, amine, formaldehyde and advantageously water and/or acid and/or base is kept at the reaction temperature and the reaction pressure during the reaction time.

In one preferred embodiment, a mixture (advantageously equimolar mixture) of formaldehyde and propanal can be heated by way of a heat exchanger to the desired reaction temperature and passed into a tubular reactor. A catalyst solution (solution of the secondary amine and of an acid, advantageously in $H_2O$) optionally heated by way of a heat exchanger likewise to the reaction temperature can be injected at the reactor inlet into the said mixture. The strongly exothermic reaction begins, and the temperature of the reaction mixture increases further. It is preferable that a pressure-retention valve at the reactor outlet is used to keep the pressure under which the reaction proceeds at values such that the reaction mixture still remains liquid during the reaction time, even when temperatures in the reactor are high. After the reaction, the reaction mixture can be depressurized to atmospheric pressure and worked up. In the production of methacrolein from propanal and formaldehyde it is preferable that the reaction mixture is passed into a column for steam-stripping. The methacrolein is discharged together with water at the top of the column. The mixture is condensed and separated by way of a phase separator to give an upper and a lower phase. The upper phase comprises the methacrolein, and is reacted by oxidative esterification according to step B) to give MMA. The lower phase is composed mainly of water. It can preferably in turn be at least to some extent returned to the column in order to remove the residual methacrolein dissolved therein.

The aqueous catalyst solution can be drawn off at the bottom of the column together with the water formed in the reaction and the water of the formaldehyde solution. For the purposes of further processing, the liquid from the bottom of the column can be discarded if very little amine and/or acid is used and return of the catalyst is therefore then not worthwhile.

However, in the case of higher concentrations of amine and/or of acid in the material discharged at the bottom of the column it is also possible to carry out distillative removal of water at least to some extent and in turn to return the catalyst solution to the reactor. Another possibility is to divide the material discharged at the bottom of the column into two sub-streams in such a way that one sub-stream comprises precisely the amount of water that was formed during the reaction and introduced with the starting materials. Said sub-stream is then removed from the system, and the remaining proportion is returned to the reactor. Aqueous formaldehyde and propanal can also be separately preheated and introduced into the reactor.

The propanal used for producing methacrolein can be purchased in large quantities. The said compound can preferably be obtained by reaction of ethylene with carbon monoxide (CO) and hydrogen ($H_2$). The hydroformylation reaction generally carried out for this purpose is well known, and reference is made in this connection to standard literature, for example Kirk-Othmer Encyclopedia of Chemical Technology, John Wiley & Sons, Inc., OXO Process and Franke et al., Applied Hydroformylation, dx.doi.org/10.1021/cr3001803, Chem. Rev. 2012, 112, 5675-5732; the said publications are hereby incorporated by way of reference into the present application.

Catalysts are usually used for this reaction. Among the preferred catalysts are in particular compounds in which rhodium, iridium, palladium and/or cobalt is present, particular preference being given here to rhodium.

According to one particular embodiment, it is in particular possible to use, for the catalysis, complexes which comprise at least one phosphorus-containing compound as ligand. Preferred phosphorus-containing compounds comprise aromatic groups and at least one, particularly preferably two, phosphorus atoms. Among the phosphorus-containing compounds are in particular phosphines, phosphites, phosphinites, phosphonites. Examples of phosphines are triphenylphosphine, tris(p-tolyl)phosphine, tris(m-tolyl)phosphine, tris(o-tolyl)phosphine, tris(p-methoxy-phenyl)phosphine, tris(p-dimethylaminophenyl)phosphine, tricyclohexylphosphine, tricyclopentylphosphine, triethylphosphine, tri(1-naphthyl)phosphine, tribenzyl-phosphine, tri-n-butylphosphine, tri-t-butylphosphine. Examples of phosphites are trimethyl phosphite, triethyl phosphite, tri-n-propyl phosphite, tri-i-propyl phosphite, tri-n-butyl phosphite, triisobutyl phosphite, tri-tert-butyl phosphite, tris(2-ethylhexyl) phosphite, triphenyl phosphite, tris(2,4-di-tert-butylphenyl) phosphite, tris(2-tert-butyl-4-methoxyphenyl) phosphite, tris(2-tert-butyl-4-methylphenyl) phosphite, tris(p-cresyl) phosphite. Examples of phosphonites are methyldiethoxyphosphine, phenyl-dimethoxyphosphine, phenyldiphenoxyphosphine, 2-phenoxy-2H-dibenzo[c,e][1,2]-oxaphosphorine and its derivatives in which some or all of the hydrogen atoms have been replaced by alkyl and/or aryl moieties or halogen atoms. Commonly used phosphinite ligands are diphenyl(phenoxy)phosphine and its derivatives, diphenyl (methoxy)phosphine and diphenyl(ethoxy)phosphine.

Catalysts and ligands for the hydroformylation process are described by way of example in WO 2010/030339 A1, WO 2008/071508 A1, EP 982 314 B1, WO 2008/012128 A1, WO 2008/006633 A1, WO 2007/036424 A1, WO 2007/028660 A1, WO 2005/090276 A1, and for disclosure purposes reference is made to the said publications, and the catalysts and ligands disclosed therein are incorporated into this application. The said publications also describe reaction conditions, which are likewise incorporated into the present application.

The hydroformylation of ethene uses carbon monoxide and hydrogen, usually in the form of a mixture known as synthesis gas. The composition of the synthesis gas used for the hydroformylation process can vary widely. The molar ratio of carbon monoxide and hydrogen is generally from 2:1 to 1:2, in particular about 45:55 to 50:50.

The temperature in the hydroformylation reaction is generally in the range of about 50 to 200° C., preferably about 60 to 190° C., in particular about 90 to 190° C. The reaction is preferably carried out at a pressure in the range of about 5 to 700 bar, preferably 10 to 200 bar, in particular 15 to 60 bar. The reaction pressure can be varied, depending on the activity of the hydroformylation catalyst used.

Suitable pressure-resistant reaction apparatuses for the hydroformylation process are known to the person skilled in the art. Among these are the well-known reactors for gas-liquid reactions, e.g. gas-circulation reactors, bubble columns, etc., which can optionally have dividing internals.

Other preferred embodiments of a hydroformylation reaction are described inter alia in EP 1 294 668 B1, and the contents of the said publication are hereby incorporated by way of reference into the present application.

According to one particularly preferred embodiment, methacrolein can be produced from propanal and formaldehyde in a tandem reaction where propanal is obtained by the reaction of ethylene, carbon monoxide and hydrogen and is directly reacted with formaldehyde. This process is described in detail by Deshpande et al., Biphasic catalysis for a selective oxo-Mannich tandem synthesis of methacrolein, Journal of Molecular Catalysis A: Chemical 211 (2004) 49-53, doi:10.1016/j.molcata.2003.10.010, and in U.S. Pat. No. 7,141,702 B2, and said publications are hereby incorporated by way of reference into the present application.

Step B)

According to the invention, the methacrolein obtained in step A) is reacted in a direct oxidative esterification reaction to give MMA.

For the purposes of the present invention, a direct oxidative esterification reaction is a process in which methacrolein is reacted directly, i.e. without formation of large amounts of methacrylic acid, to give MMA in the presence of methanol and of an oxidant, preferably oxygen.

In contrast to this, in processes which are carried out by way of example by BASF, methacrolein is first oxidized to give methacrylic acid, which is then esterified in a further reaction step with methanol to give MMA.

In the process according to BASF it is possible that methanol present for stabilization purposes or present by virtue of the production process in the formaldehyde used likewise forms small amounts of MMA during the oxidation of methacrolein. However, this MMA cannot be separated from returned methacrolein by inexpensive purification processes, and generally decomposes under the selected conditions; this therefore reduces the final yield of MMA from methanol present in the formaldehyde. To solve this problem, a complicated method must be used to free formaldehyde from methanol. Alternatively, it is certainly possible to use a purification step to remove the MMA present in the composition intended for return, but both solutions incur high cost, which is uneconomic because the amounts of MMA attained are relatively small.

Oxidation of methacrolein in an oxidative esterification reaction according to step B) of the process of the present invention generally produces at most 30% by weight, preferably at most 15% by weight, particularly preferably at most 5% by weight, of methacrylic acid.

An oxidative esterification reaction is carried out with an oxidant, and it is preferable to use oxygen ($O_2$) for this purpose. For reasons of cost, air can preferably be used, and can comprise different proportions of oxygen; this would not be critical for the present invention.

At least one heterogeneous oxidation catalyst is moreover used for carrying out a reaction according to step B), and these selectively accelerate the oxidation reaction defined in more detail above. Suitable catalysts are well known to persons skilled in the art and are described by way of example in the publications EP 0 857 512 A1, EP 1 393 800 A1, EP 2 177 267 A1, and EP 2 210 664 A1, and reference is made to the said publications for disclosure purposes, and the catalysts disclosed therein are incorporated into this application. Said publications also describe reaction conditions, which are likewise incorporated into the present application.

Heterogeneous oxidation catalysts preferably comprise at least one noble metal and/or at least one metal oxide. Preference is given here to oxidation catalysts in which gold and/or palladium and/or ruthenium and/or rhodium and/or silver is present. Gold- and/or palladium-containing catalysts are particularly preferred.

Among the suitable catalysts for carrying out the present process are inter alia palladium catalysts, where these preferably comprise palladium and lead and are generally used on a support.

A palladium catalyst can also comprise at least one compound selected from the group consisting of an alkali metal compound and of an alkaline earth metal compound. It is preferable that a palladium catalyst comprises from 0.01 to 30% by weight, more advantageously from 0.01 to 5% by weight, of at least one compound selected from the group which consists of an alkali metal compound and of an alkaline earth metal compound.

The introduction of the alkali metal compound and/or of the alkaline earth metal compound into the catalyst can be carried out by a process in which a compound of this type is added to a solution in which a palladium compound and/or a lead compound is present, and a support is treated with the solution, whereupon the alkali metal compound and/or the alkaline earth metal compound, together with the palladium compound and/or with the lead compound, is adsorbed onto the support or adheres thereto. Alternatively, a support which comprises an alkali metal compound and/or an alkaline earth metal compound adsorbed thereon can be used for producing a catalyst. Another possibility, instead of the use of a support, is that a solution in which an alkali metal compound and/or an alkaline earth metal compound is present is added to the reaction mixture during the reaction according to step B).

The amount of the palladium supported on the support is not subject to any particular restriction, but the amount is preferably from 0.1 to 20% by weight, more preferably from 1 to 10% by weight, based on the weight of the support. The amount of the lead supported on the support is not subject to any particular restriction, but the amount is preferably from 0.05 to 17% by weight, more preferably from 0.45 to 8.5% by weight, based on the weight of the support. The atomic ratio of palladium to lead is preferably in the range from 3:0.7 to 3:1.3, more preferably in the range from 3:0.9 to 3:1.1.

A disadvantage of the palladium catalysts described above is that the lead usually present can cause environmental harm and therefore that wastewater requires complicated treatment to remove lead residues.

In an alternative embodiment, a catalyst used for the oxidative esterification comprises minimized amounts of lead. Accordingly, the oxidative esterification reaction according to step B) can be carried out with use of a catalyst of which the lead content is preferably at most 20% by weight, with preference at most 10% by weight, specifically preferably at most 5% by weight, particularly preferably at most 2% by weight and very particularly preferably at most 1% by weight. According to one specifically preferred embodiment, step B) uses a catalyst which preferably comprises at most 1.5% by weight, with preference at most 1% by weight, specifically preferably at most 0.5% by weight, particularly preferably at most 0.2% by weight and very particularly preferably at most 0.1% by weight, of lead. Step B) can moreover use a catalyst which comprises no measureable content of lead.

It can also be provided that the oxidative esterification reaction according to step B) is carried out with use of a catalyst which comprises one or more metals selected from the group consisting of gold and/or palladium and/or ruthenium and/or rhodium and/or silver. It is preferable that said metals take the form of ultra-finely dispersed metals, i.e. take the form of nanoparticles, applied to a support. The average diameter of the metal particles is preferably at most 20 nm, preferably at most 10 nm, particularly preferably 5 nm, where said value is based on a numeric average determined by TEM (Transmission Electron Microscopy). The "average diameter" of the particles is calculated from the diameter of 100 particles selected from 120 particles, where the ten largest particles and the ten smallest particles of the 120 particles are ignored.

A preferred catalyst can comprise other catalytically active constituents alongside gold particles and/or palladium particles and/or ruthenium particles and/or rhodium particles and/or silver particles. Among the other catalytically active constituents are inter alia magnesium, scandium, yttrium, lanthanum and other lanthanoids with atomic numbers from 58 to 71, titanium, zirconium, hafnium, vanadium, niobium, tantalum, chromium, molybdenum, tungsten, manganese, rhenium, iron, osmium, cobalt, iridium, nickel, platinum, copper, zinc, cadmium, aluminium, gallium, indium, thallium, germanium, tin, lead, antimony, and bismuth, these being able to be respectively present in metallic and/or oxidized form (e.g. in the form of oxides, hydroxides, or salts). Said other catalytically active constituents take the form of particles which preferably have an average diameter of at most 20 nm, with preference at most 10 nm, with particular preference at most 5 nm. It is possible here that the gold particles and/or palladium particles and/or ruthenium particles and/or rhodium particles and/or silver particles and the particles with other catalytically active constituents are present together or separately, in particular in alloyed or non-alloyed form, on the support. It is preferable that the gold particles and/or palladium particles and/or ruthenium particles and/or rhodium particles and/or silver particles comprise the other catalytically active constituents.

The proportion of the catalytically active particles of the catalyst can vary widely. The proportions of the catalytically active particles are preferably in the range of about 0.01 to 20 parts by weight, particularly preferably in the range from 0.1 to 10 parts by weight, per 100 parts by weight of the catalyst.

If the catalyst comprises, alongside gold particles, other elements in the form of catalytically active components, the atomic ratio of gold to the entirety of the other elements can be in the range from 1:0.001 to 1:1000, preferably from 1:0.01 to 1:100, particularly preferably from 1:0.1 to 1:10 and specifically preferably from 1:0.2 to 1:5.

It can also be provided that the oxidative esterification reaction according to step B) is carried out with use of a nickel-containing catalyst. It is preferable that nickel-containing catalysts comprise content of a noble metal, preferably gold. It is preferable that nickel-containing catalysts comprise nickel oxide, which is used in combination with nickel, palladium, platinum, ruthenium, gold, silver and/or copper. It is preferable that the atomic ratio of $NiO_x$ to ($NiO_x$+X) is in the range from 0.20 to 0.99, preferably from 0.30 to 0.90 and particularly preferably from 0.50 to 0.90, where X is selected from nickel, palladium, platinum, ruthenium, gold, silver and/or copper, particular preference being given here to gold. In this formula, $NiO_x$ is present as oxide, while X is present in metallic form. Nickel oxide $(NiO)_x$ can by way of example take the form of $Ni_2O$, $NiO$, $NiO_2$, $Ni_3O_4$ or $Ni_2O_3$.

The nickel oxide and other components, in particular metallic components, such as nickel, palladium, platinum, ruthenium, gold, silver and/or copper, here can preferably be used in the form of nanoparticles with a size in the range from 2 to 15 nm, preferably from 2 to 10 nm and particularly preferably from 2 to 6 nm, where this value refers to a numeric average determined by TEM (Transmission Electron Microscopy), as defined in more detail above. The nanoparticles are preferably fixed on a support.

The catalysts described above are generally applied on a support, where the said supports can comprise metal oxides (e.g. silicon dioxide, aluminium oxide, titanium oxide, zirconium oxide, or magnesium oxide), mixed oxides (such as silicon dioxide-aluminium oxide, titanium dioxide-silicon dioxide or silicon dioxide-magnesium oxide), zeolites (such as ZSM-5), mesoporous silicates (such as MCM-41), natural minerals (such as clay, diatomaceous earth or pumice), or carbon materials (e.g. activated charcoal or graphite). It is preferable to use inorganic supports based on oxides.

It is particularly advantageous to use an inorganic support based on oxides and comprising silicon, lithium, sodium, potassium, magnesium, calcium, scandium, yttrium, lanthanum and other lanthanoids with atomic numbers from 58 to 71, titanium, zirconium, hafnium, vanadium, niobium, tantalum, chromium, molybdenum, tungsten, manganese, rhenium, iron, ruthenium, osmium, cobalt, rhodium, iridium, nickel, platinum, palladium, copper, silver, zinc, cadmium, boron, aluminium, gallium, indium, thallium, germanium, tin, lead, antimony, bismuth and/or tellurium.

A preferred support based on oxides comprises silicon oxide as main component and one or more members of the group consisting of lithium, sodium, potassium, magnesium, calcium, scandium, yttrium, lanthanum and other lanthanoids with atomic numbers from 58 to 71, titanium, zirconium, hafnium, vanadium, niobium, tantalum, chromium, molybdenum, tungsten, manganese, iron, cobalt, nickel, copper, silver, zinc, cadmium, aluminium, gallium, indium, thallium, germanium, tin, lead, antimony and bismuth.

The process for producing the abovementioned inorganic supports based on oxides is not subject to any particular restrictions, and it is possible to use any known production process. Examples comprise impregnation, coprecipitation, ion exchange, gas-phase deposition, kneading and hydrothermal synthesis.

It is preferable to use a porous support. It is particularly preferable that the specific surface area (BET method) is generally at least 50 m$^2$/g, with preference at least 100 m$^2$/g.

The process for loading the support with the catalytically active constituents is not subject to any particular restrictions. Suitable processes are inter alia coprecipitation, precipitative deposition, impregnation and vapour-phase deposition.

The catalysts described above based on gold and/or nickel oxide are preferred over the palladium catalysts. Nickel-containing and gold-containing catalysts can preferably be lead-free.

It can preferably be provided that the water content of the reaction mixture used for the oxidative esterification in step B) is preferably at most 10% by weight and with preference at most 5% by weight.

The said low proportions of water can optionally be achieved by using a phase separator, and the water content of the methacrolein phase can vary here as a function of temperature. Accordingly, it is preferable that the reaction mixture obtained after the reaction of formaldehyde with propanal is cooled to a temperature at which the water content in the methacrolein phase adopts the values mentioned. The temperature in the phase separator can preferably be adjusted to from 0 to 50° C., preferably from 5 to 30° C. and particularly preferably from 10 to 25° C. However, removal of the water is only necessary at particularly high water contents of more than 10% by weight, to the extent that a marked increase in space-time yield can be achieved. In the case of water contents above 5% by weight, a small methyl methacrylate yield increase can be achieved by removing water until content is below 5% by weight.

Equally surprisingly, it has been found that, contrary to the assumptions made in the prior art, high methyl methacrylate space-time yields can also be achieved with residual content of starting materials or by-products from step A): although propanal, formaldehyde and dimeric methacrolein are reacted to give methyl propionate, methyl formate and the methyl ester of oxidized dimeric methacrolein, this formation of by-products is the only adverse effect of these components on the entire process. Surprisingly, therefore, the total yield of MMA is very high, and the by-products mentioned can easily be removed during MMA work-up.

It is also preferable that the content of methacrolein in the reaction mixture used for the oxidative esterification in step B) is at least 5% by weight, preferably at least 15% by weight and particularly preferably at least 25% by weight.

It can also be provided that the oxidative esterification reaction according to step B) preferably takes place with a molar ratio of methanol to methacrolein in the range from 1:1 to 50:1, particularly preferably from 1.5:1 to 25:1 and specifically preferably from 2:1 to 10:1.

The amount of the catalyst to be used varies, depending on the composition of the feed mixture and of the catalyst, on the reaction conditions, and on the types of reaction and the like. If the catalyst used takes the form of a slurry, it is preferable that the amount used of the catalyst is from 0.01 to 0.5 kg/l of the reaction system solution.

The oxidative esterification reaction can be carried out in any conventional manner, for example in a liquid-phase reaction or trickle-bed reaction. By way of example, it is possible to use any known reactor, e.g. a bubble-column reactor, a tubular reactor with air stream or a stirred reactor.

The pressure at which the said reaction is carried out can vary widely. Surprising advantages can be achieved through a reaction pressure in the range from 2 to 100 bar, preferably from 3 to 80 bar, more preferably from 4 to 50 bar and particularly preferably from 5 to 20 bar.

It is preferable to keep the reaction system at a pH of from 5 to 9, particularly from 6.5 to 8, by adding at least one basic compound preferably selected from the group consisting of an alkali metal compound and/or an alkaline earth metal compound, for example an oxide, hydroxide, carbonate, carboxylate or the like.

The oxidative esterification reaction according to step B) can take place at a temperature in the range of preferably 10° C. to 200° C., particularly preferably 40 to 150° C. and specifically preferably 60 to 120° C.

The reaction time or residence time varies, depending on other reaction conditions; however, it is preferably in the range from 10 minutes to 48 hours, with preference from 30 minutes to 24 hours and particularly preferably from 45 minutes to 2 hours.

Further information concerning the conduct of an oxidative esterification reaction according to step B) for MMA synthesis is found inter alia in U.S. Pat. No. 4,249,019 or DE 3018071A1.

Oxidative esterification under the conditions mentioned above gives a reaction mixture which comprises MMA as main reaction product. The resultant reaction mixture also comprises, in addition to MMA, unreacted methacrolein and unreacted methanol and small amounts of water and methacrylic acid as by-products. The reaction mixture also comprises traces of other by-products, which comprise dimethacrolein and the like.

The reaction product obtained in step B) can be worked up in a known manner in order to obtain pure MMA: the reacted reaction mixture obtained through the oxidative esterification according to step B) can first be worked up by distillation.

According to one preferred embodiment, the reaction mixture can be passed into a distillation tower, and is preferably passed into the central portion thereof: it is generally possible to discharge an azeotropic mixture of methacrolein and methanol as overhead distillation product.

A mixture comprising liquid MMA, methanol, water and other by-products is obtained from the bottom of the distillation tower. Said liquid mixture is purified by a conventional process. Said purification unit can generally comprise at least one, preferably two or more, distillation systems for removing high-boiling-point and low-boiling-point compounds.

In the present invention, the nature of the distillation tower that is preferably used for work-up of the reaction mixture obtained from the oxidative esterification is not subject to any particular restriction, and it is possible to use any desired conventional distillation tower, for example a plate column or a packed column.

However, since methacrolein, MMA and methacrylic acid, which are passed into the distillation tower, are readily polymerizable compounds it is preferable to use a distillation system with a structure where blockage by polymerization products does not occur and/or the polymerization products can easily be removed. Specific examples of distillation towers comprise plate columns equipped with a sieve tray, cascade tray, turbogrid tray, grooved tray or the like, and packed columns with ordered packing materials (e.g. Mellapak from Sulzer) or with unordered packing materials (e.g. Raschig Superring from Raschig).

The suitable distillation temperature in the distillation tower preferably used in the claimed process for work-up of the reaction mixture obtained from the oxidative esterification varies as a function of the distillation pressure, of the composition of the liquid in the distillation tower, of the number of plates in the distillation tower and the like. However, in order to minimize the formation of the above-mentioned polymerization products and the formation of high-boiling-point compounds which represent a yield loss, based on methacrolein or MMA, it is preferable that the distillation temperature is minimized. However, if a very low distillation temperature is selected disadvantages can arise. Among these are, by way of example, that a low distillation pressure also has to be selected. This can require use of a disadvantageously large distillation tower. It can moreover be necessary to use a coolant for concentrating the gas phase in the uppermost portion of the distillation tower. It is preferable that the distillation temperature, or the temperature of the liquid in the column, is in the range from 20 to 100° C., particularly from 40 to 85° C. The distillation pressure is calculated from said temperature.

As mentioned previously, methacrolein, MMA and optionally other polymerizable by-products, such as methacrylic acid, can be passed into a distillation tower in order to separate the reaction product of the oxidative esterification into methanol/methacrolein mixtures and MMA/water mixtures.

Because polymers can be formed, it is preferable that one or more polymerization inhibitors is/are added to the process. Polymerization inhibitors are well known to persons skilled in the art, examples being hydroquinones, hydroquinone ethers, such as hydroquinone monomethyl ether or di-tert-butylpyrocatechol, phenothiazine, N,N'-diphenyl-p-phenylenediamine, 4-hydroxy-2,2,6,6-tetramethylpiperidin-1-oxyl, p-phenylenediamine, methylene blue and sterically hindered phenols. The said compounds can be used individually or in the form of mixtures and are generally available commercially. The action of the stabilizers mostly consists in their action as free-radical scavengers for the free radicals arising during polymerization. Reference is made to the familiar technical literature for further details, in particular to Römpp-Lexikon Chemie [Römpp's Chemical Encyclopaedia]; Editors: J. Falbe, M. Regitz; Stuttgart, New York; 10th Edition (1996); keyword "Antioxidantien" [Antioxidants] and to the references there cited.

In particular, phenols are preferably used as polymerization inhibitor. Particularly surprising advantages can be achieved when hydroquinone monomethyl ether is used. The proportion of the inhibitors, individually or in the form of a mixture, can generally be from 0.001 to 0.5% by weight, based on the weight of the entire composition.

It is preferable that steps A) and B) are carried out in a continuous process. Introduction of starting materials into the plant for carrying out a process according to the present invention, and removal of products from the plant, take place here continuously over any desired period. Said period can be interrupted for maintenance and repair work, however.

It can also be provided that the reactor volume in step A) is smaller than the reactor volume in step B). The reactor volume here is based on the volumes in step A) and step B), where the starting materials used within these are reacted in the liquid phase under the elevated pressure of the respective reaction to give the products.

The ratio of reactor volume in step A) to reactor volume in step B) is advantageously in the range from 1:1000 to 1:100, preferably in the range from 1:800 to 1:200 and particularly preferably in the range from 1:500 to 1:300.

Typical reactor volumes for a continuously operated production plant can by way of example be for step A) a tubular/tube-bundle reactor of capacity from 0.1 to 0.5 $m^3$ and for step B) a tubular/tube-bundle reactor of capacity from 10 to 15 $m^3$ or a continuously operated stirred tank of capacity from 50 to 100 $m^3$, but these data are not intended to represent any restriction.

Surprisingly, when the present process is compared with conventional processes which oxidize C4 building blocks such as isobutylene, it successfully achieves a marked reduction in the volume to be compressed, in particular of gas.

In the claimed process, composed of the combination of the reaction steps A) and B), there is no essential requirement in any of the individual reaction steps to introduce into the reaction mixture additional water, i.e. water that is not already present by virtue of other circumstances in the reactants. This is a decisive advantage over the prior art, since additionally introduced water enlarges the reaction streams and therefore also enlarges the necessary apparatuses, and generally also in turn requires removal from the desired final products, with resultant additional energy cost and other costs. Overall reaction volumes and volume flow rates can therefore be kept low in the claimed process.

The Asahi process according to U.S. Pat. Nos. 5,969,178 and 7,012,039 requires by way of example during the gas-phase oxidation of the $C_4$-component the addition and in turn subsequent removal of a stoichiometric excess of water. The processes known hitherto for producing methacrolein from ethylene by way of propionaldehyde, then oxidizing this to methacrylic acid and then esterifying to MMA require the addition of a stoichiometric excess of water during the gas-phase oxidation of the methacrolein to methacrylic acid, in order to ensure that the activity of the oxidation catalyst is maintained.

In the claimed process, composed of the combination of the reaction steps A) and B), the total amount of water separately added during conduct of the reaction is therefore not greater than 100 mol %, preferably 50 mol %, particularly preferably 30 mol %, and even more preferably not greater than 10 mol %, based in each case on methacrolein. In one particularly advantageous embodiment of the claimed process, no water is separately added to the reaction mixture in either of the reaction steps A) and B) during the conduct of the reaction. Water of reaction and water addition for work-up steps are always excluded here.

Figure 1:
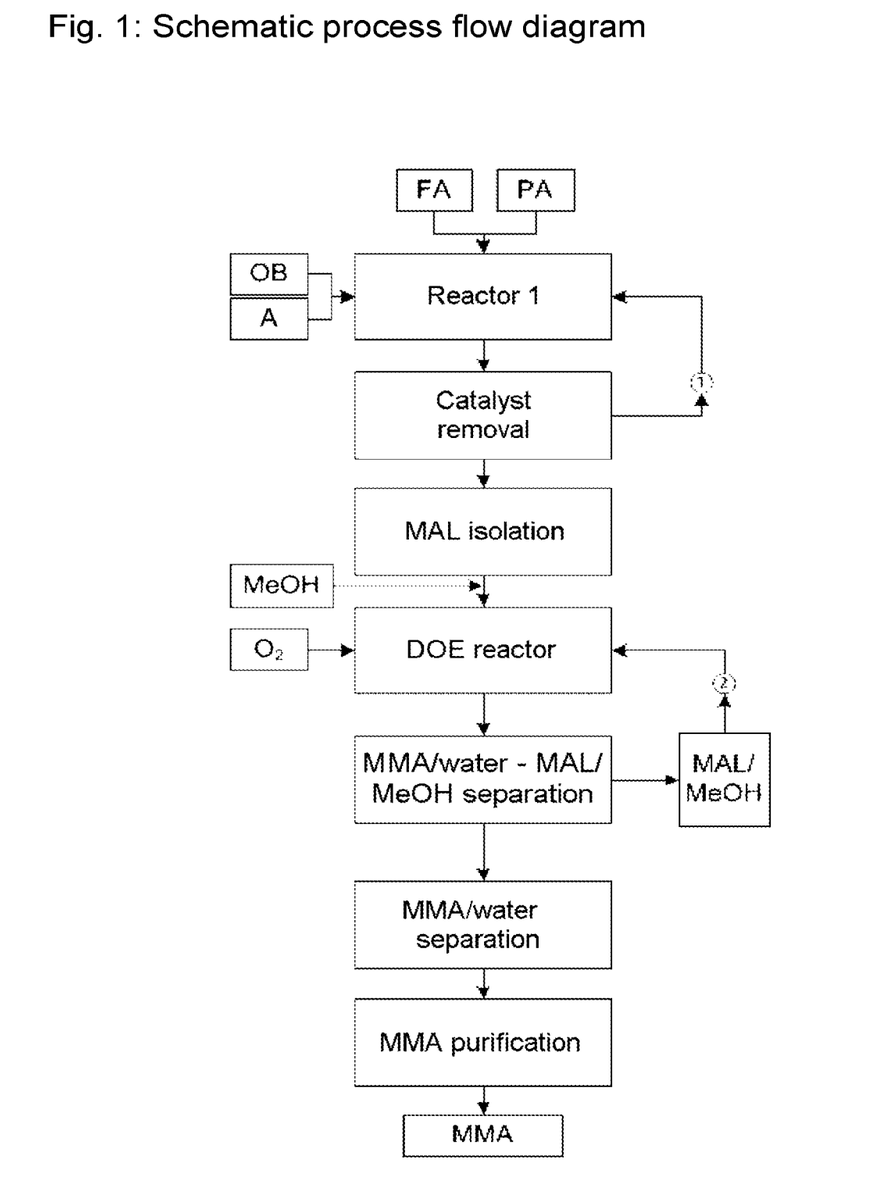
Fig. 1: Schematic process flow diagram

FIG. 1 is by way of example a diagram of the claimed process, but is not intended to restrict the invention.

Formaldehyde (FA) and propanal (PA) are introduced after premixing or individually into the reactor 1, and similarly the organic base (OB) and the acid catalyst (A) are introduced after premixing or individually into the reactor. After aldol condensation and catalyst removal, the methacrolein (MAL) is isolated. The catalyst can be returned to the reactor 1 by way of stream (1). The MAL and methanol (MeOH) are introduced into the oxidative esterification reactor (DOE reactor). An oxygen-containing gas ($O_2$) is fed into the said reactor. The unreacted MAL from the esterification reactor is removed in the form of MAL/methanol azeotrope in an MMA/water-MAL/MeOH separation process, and is returned to the DOE reactor by way of stream (2). An MMA/water separation process and further purification of the crude MMA then follow.

Figure 2:
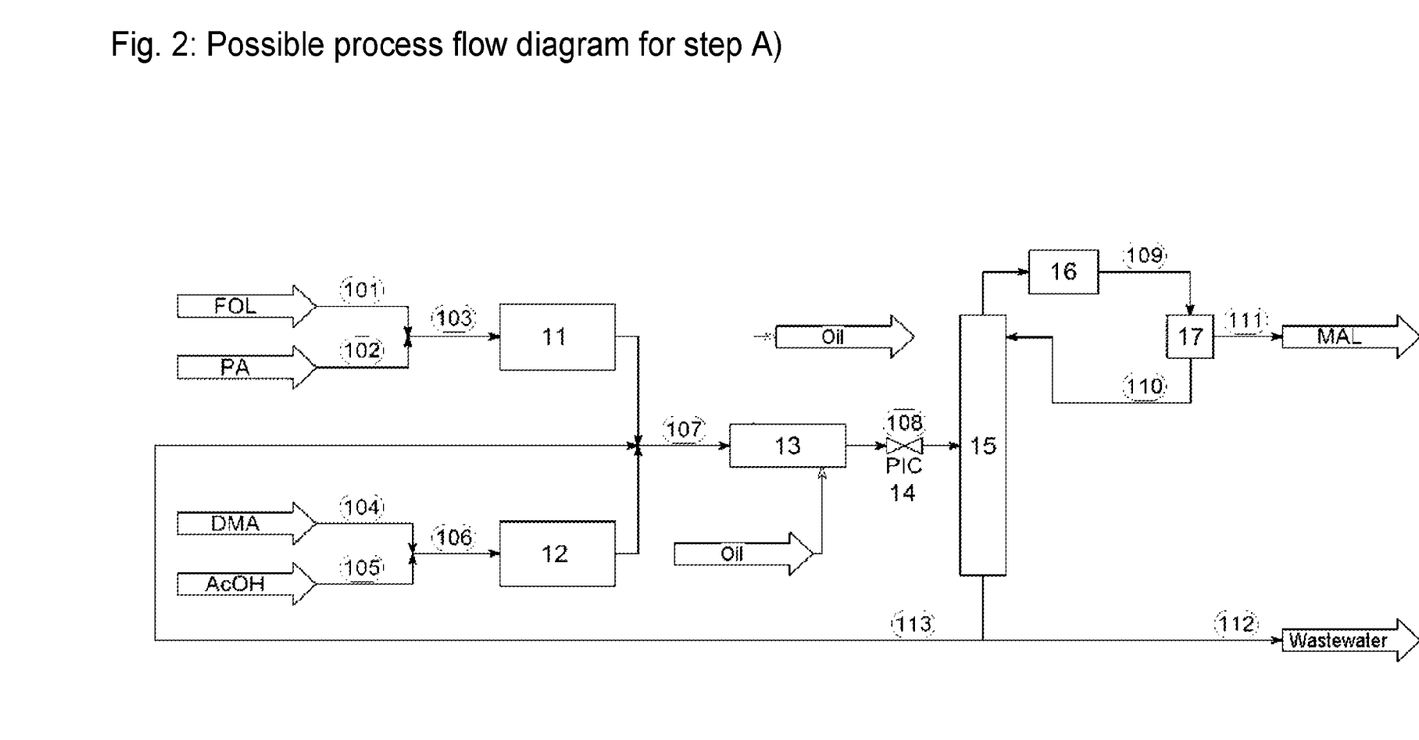
Fig. 2: Possible process flow diagram for step A)

FIG. 2 shows a possible system for the reaction of formaldehyde with propanal to give methacrolein (step A). Aqueous formalin (101) is mixed with propionaldehyde (102) and passed in the form of stream (103) into the preheater (11). Dimethylamine (40% aqueous solution) (104) and acetic acid (105) are mixed and passed in the form of stream (106) into the preheater (12). Operation of the preheaters (11) and (12) is optional. The mixture from the outlets of (11) and (12) is introduced in the form of stream (107) into the tubular reactor (13). The tubular reactor (13) is heated by means of an oil bath to the reaction temperature. Downstream of the tubular reactor, the mixture (108) is depressurized in valve (14) and introduced into the column (15). The material discharged from the bottom of the column is divided (50/50), and one portion is returned to the stream (107) into the reactor (13), the other portion being passed for disposal in the form of wastewater stream (112). The stream obtained at the top of the column is condensed in the condenser (16) and is introduced in the form of stream (109) into the phase separator (17). A methacrolein-rich phase (111) in the said phase separator is discharged as product into the "direct oxidative esterification" portion of the system according to FIG. 3, and the stream (111) here can optionally be dried by azeotropic distillation (not shown).

The aqueous discharge from the phase separator (17) is returned in the form of stream (110) to the column (15).

Figure 3:
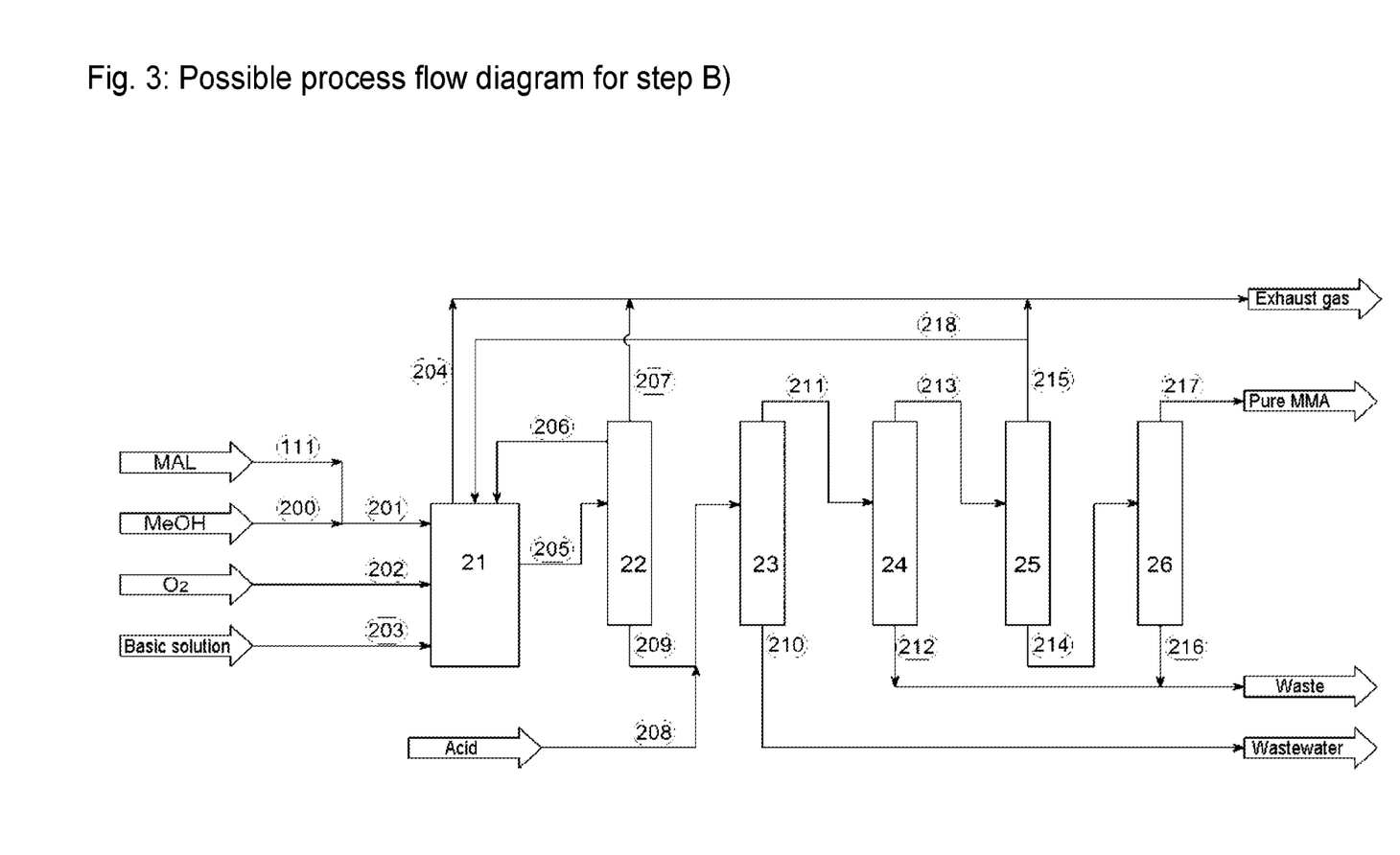
Fig. 3: Possible process flow diagram for step B)

FIG. 3 shows a possible apparatus which can produce MMA from MAL and which is suitable for carrying out the direct oxidative esterification (step B). Methanol is introduced by way of supply line (200) to the line (111) by way of which methacrolein is taken from step A) of the process. Air (or oxygen-containing gas mixture) is passed by way of the supply line (202) into the reactor (21), which comprises a catalyst suitable for the direct oxidative esterification process, and a basic composition which preferably comprises methanol and NaOH is also passed by way of the supply line (203) into the reactor (21) in order to adjust pH. FIG. 3 does not show the ancillary assemblies, such as pumps, heating elements, heat exchangers and condensers. It is also optionally possible to use a plurality of reactors (21) connected in series (not shown).

Exhaust gases are discharged from the reactor (21) through the exhaust-gas scrubber by way of line (204), and methanol, MMA and methacrolein here can be at least to some extent condensed in one or more condensers and returned to the reactor (21) (not shown).

The reaction mixture present in the reactor (21) is passed by way of line (205) to the distillation column (22), and methacrolein (or methacrolein-containing mixture) here is returned by way of line (206) to the reactor (21). Gases and other low-boiling-point components can be removed from the reaction mixture at the top of the distillation column (22) and introduced by way of line (207) into the exhaust gas. The composition taken by way of line (209) from the material at the bottom of the distillation column (22) in essence comprises MMA, which can comprise methanol, methacrylic acid, sodium methacrylate and other components.

An acid or acid-containing mixture, for example aqueous sulphuric acid, can be passed by way of supply line (208) from a feed vessel to the line (209). The resultant mixture is passed to a water/oil separation system (23) which by way of example can comprise a centrifuge, and is separated into aqueous and organic phase. At this point it is possible to connect a plurality of similar water/oil separation systems in parallel, so that these can be operated in alternation as required (not shown). The aqueous phase from the separation system (23) can be introduced by way of line (210) into a wastewater treatment system, while the organic phase is introduced by way of line (211) to the distillation column (24) for removal of the high-boiling-point components. High-boiling-point components, e.g. methacrylic acid, can be taken from the material at the bottom of the said column (24) by way of line (212) for further post-treatment. Crude MMA is taken from the top of the column (24) by way of line (213) and introduced into the column (25). The low-boiling-point components (e.g. methanol and methacrolein) can be taken from the top of the said column by way of line (215) and returned by way of line (218) to the reactor (21), and a portion thereof can be discharged and introduced into the exhaust-gas stream (204). Purified MMA can be taken from the material at the bottom of the column (25) by way of line (214) and can be introduced into the final column for MMA purification (26). Pure MMA is taken from the top of the column by way of line (217), while the remaining high-boiling-point components can be taken from the material at the bottom of the column by way of line (216) for further post-treatment or for return upstream of column (24) (not shown).

Key
FIG. 1
OB Organic base
A Acid
MeOH Methanol
O$_2$ Oxygen-containing gas
MMA Methyl methacrylate
FA Formalin (aqueous formaldehyde solution)
PA Propanal
MAL Methacrolein
DOE Direct oxidative esterification
① Catalyst return
② Methacrolein/methanol return
FIG. 2
FOL Formalin (aqueous formaldehyde solution)
PA Propanal
DMA Aqueous dimethylamine solution
AcOH Acetic acid
MAL Methacrolein
11 Heat exchanger (preheater)
12 Heat exchanger (preheater)
13 Reactor (tubular reactor)
14 Pressure-retention valve
15 MAL distillation column
16 Condenser
17 Phase separator
101 Aqueous formalin line
102 Propanal line
103 Line leading to heat exchanger
104 Dimethylamine (40% aqueous solution) line
105 Acetic acid line
106 Line leading to heat exchanger
107 Line leading to reactor
108 Line taking product mixture to column
109 Condensate line
110 Return to column
111 MAL to stage B)
112 Line leading to wastewater system
113 Return of material discharged from bottom of column
FIG. 3
MAL Methacrolein
MeOH Methanol
O$_2$ Oxygen-containing gas
MMA Methyl methacrylate
21 Reactor
22 MAL removal
23 Water/oil separation
24 Removal of high-boiling-point materials
25 Removal of low-boiling-point materials
26 Final purification of MMA
111 MAL from stage A)
200 Methanol supply line
201 MAL/methanol supply line
202 Supply line for oxygen-containing gas
203 Supply line for basic composition
204 Exhaust-gas stream
205 Product stream to column 22
206 MAL return
207 Exhaust-gas stream
208 Acid supply line
209 Product stream to water/oil separation system
210 Aqueous phase discharge line
211 Product stream to column 24
212 Discharge line for high-boiling-point materials
213 Product stream to column 25
214 Product stream to column 26
215 Discharge line for low-boiling-point materials 216 Discharge from bottom of column
217 Pure MMA line
218 Return of low-boiling-point materials The examples below serve for further explanation of preferred embodiments of the present invention, but are not intended to restrict the invention.

EXAMPLE 1

In a system corresponding to FIG. 2, propanal (PA) is reacted continuously with formaldehyde with use of dimethylamine (DMA) and acetic acid (AcOH). 251 g/h of PA and 349 g/h of a 37 percent formalin solution are premixed homogeneously (molar ratio 1:1). 18.7 g/h of a catalyst solution with 24.8% of dimethylamine and 37.9% of acetic acid are passed into the preheater 12. The two streams are heated to a temperature of 170° C. before they are combined. The preheated streams are combined in a T mixer which has direct connection to a tubular reactor (1/16 inch tube, length 4.2 m). The temperature of the reactor is controlled by an oil bath operated at 180° C., residence time is 10 s, and the pressure in the tubular reactor is 70 bar. Downstream of the tubular reactor, the mixture is depressurized in valve (14) and is introduced into the column (15). 335 g/h of the material discharged at the bottom of the column are returned to the reactor (13), and 370 g/h of the material discharged at the bottom of the column are passed for disposal in the form of wastewater. After condensation of the overhead stream in the condenser (16) and phase separation in (17), a methacrolein-rich phase with 96.5% methacrolein content is discharged as product (111), and the aqueous material discharged from the phase separator is returned to the column (15). Conversion is 99.9% and yield is 98.1%, based on propionaldehyde. The residual water content of the methacrolein used in Examples 2 to 4 was 1.7% by weight.

EXAMPLE 2

Catalyst 1 (0.9% Au-1.1% NiO on $SiO_2$—$Al_2O_3$—MgO) was produced by analogy with Example 1 of EP 2 210 664 A1. A solution of 375 g of aluminium nitrate nonahydrate, 256 g of magnesium nitrate hexahydrate and 54 g of 60% nitric acid in 500 mL of water was added dropwise at 15° C. to 2 kg of silica sol solution with particle size from 10 to 20 nm (Nissan Chemical Industries, Snowdex N-30, 30 wt % $SiO_2$). The mixture was stirred at 50° C. for 24 hours, then cooled to room temperature, spray-dried (130° C.) and calcined (300 to 600° C., 10 hours in total). 30 g of this $SiO_2$—$Al_2O_3$—MgO support were suspended in 100 mL of water and heated to 90° C. After 15 min at 90° C., this suspension was added to a solution of 1.64 g of nickel nitrate hexahydrate and 530 mg of auric acid ($HAuCl_4$) in 100 mL of water. After stirring at 90° C. for a further 30 minutes, the mixture was cooled and the solid was removed, then washed three times with 100 mL of fresh water and in each case stirred at 20° C. for 5 minutes and filtered off. The catalyst was dried at 105° C. within a period of 10 hours and calcined at 450° C. within a period of 5 hours in air. ICP analysis showed that the resultant violet powder comprised 1.1% of Ni and 0.9% of Au. The average size of gold nanoparticles (TEM) was less than 5 nm.

A mixture of 0.67 g of methacrolein (from Example 1), 5.65 g of methanol and 504 mg of Au catalyst 1 was stirred in an autoclave under 11 bar of an $O_2/N_2$ gas mixture (7% by volume of $O_2$) at 80° C. within a period of 2 hours, and then cooled and filtered and analysed by means of GC. MAL conversion was 98.4%, MMA yield was 94.8%, MMA selectivity was 96.3%, and space-time yield was 9.3 mol MMA/kg cat-h.

EXAMPLE 3

Catalyst 2 (1% Au-5% ZnO-5% MgO on $SiO_2$) was produced by analogy with Example 1-6 of EP1393800A1. 89 g of a commercially available $SiO_2$ support (Cariact Q-10, 75-150 μm, Fuji Silisia) was impregnated with a solution of 18.3 g of zinc nitrate hexahydrate and 12.8 g of magnesium nitrate hexahydrate in 90 mL of water, dried at 120° C. within a period of 12 hours, and then calcined at 600° C. within a period of 4 hours. 300 mL of a 20 mmol/L solution of $HAuCl_4$ were adjusted with a 0.5 M solution of NaOH at 70° C. to pH=7, and the previously produced $SiO_2$—ZnO—MgO support was added at the said temperature, with stirring. After further stirring at 70° C. for one hour, the mixture was cooled and filtered, and the catalyst was washed three times with 400 mL of fresh water, being stirred in each case at 20° C. for 5 minutes. After drying at 100° C. for 10 hours, the material was calcined at 400° C. within a period of 3 hours in air. ICP analysis showed that the resultant violet powder comprised 1.5% Au. The average size of gold nanoparticles was less than 5 nm.

A mixture of 0.60 g of methacrolein (from Example 1), 5.76 g of methanol and 300 mg of catalyst 2 was stirred in an autoclave under 11 bar of an $O_2/N_2$ gas mixture (7% by volume of $O_2$) at 80° C. within a period of 2 hours, and then cooled and filtered and analysed by means of GC. MAL conversion was 85.5%, MMA yield was 83.4%, MMA selectivity was 97.5%, and space-time yield was 14.0 mol MMA/kg cat-h.

EXAMPLE 4

Catalyst 3 (1.5% Au-5% $La_2O_3$-5% MgO on $SiO_2$) was produced by analogy with Example 1-7 of EP1393800A1. 88.5 g of a commercially available $SiO_2$ support (Cariact Q-10, 75-150 μm, Fuji Silisia) was impregnated with a solution of 13.3 g of lanthanum nitrate hexahydrate and 12.8 g of magnesium nitrate hexahydrate in 90 mL of water, dried at 120° C. within a period of 12 hours, and then calcined at 600° C. within a period of 4 hours. 450 mL of a 20 mmol/L solution of $HAuCl_4$ were adjusted with a 0.5 M solution of NaOH at 70° C. to pH=7, and the previously produced $SiO_2$—$La_2O_3$ support was added at the said temperature, with stirring. After further stirring at 70° C. for one hour, the mixture was cooled and filtered, and the catalyst was washed three times with 400 mL of fresh water, being stirred in each case at 20° C. for 5 minutes. After drying at 100° C. for 10 hours, the material was calcined at 400° C. within a period of 3 hours in air. ICP analysis showed that the resultant violet powder comprised 1.5% Au. The average size of gold nanoparticles was less than 5 nm.

A 42.9% solution of methacrolein (from Example 1) in methanol was introduced continuously at a flow rate of 420 g/h into a mechanically stirred 2.5 L stirred-tank reactor with a catalyst separator to which 255 g of catalyst 3 had been charged. An NaOH solution in methanol (from 1 to 4% by weight) was added at a flow rate of 40 g/h to maintain the pH of the reaction mixture at about 7. The amount of air introduced continuously into the reactor at 5 bar and 80° C. was sufficient to give a residual proportion of oxygen in the exhaust gas of about 4% by volume of $O_2$. The product mixture taken continuously from the system was analysed by means of GC. 50 h after the start of the process, methacrolein conversion was 78.5%, MMA yield was 76.5%, MMA selectivity was 97.4%, and space-time yield was 9.8 mol MMA/kg cat-h. The reaction mixture obtained in the reactor (21) was introduced at level 30 (from above) into the distillation column (22) (45 levels, diameter 15 cm, height 6 m). The temperature of the material at the bottom of the column was 84° C., and the overhead temperature was 31° C. The methacrolein/methanol mixture was taken from the column at level 5 (from above) and returned to the reactor (21). The composition taken from the material at the bottom of the distillation column (22) at a flow rate of 500 g/h was composed of MMA which also comprised methanol, methacrylic acid, sodium methacrylate and other components. The amount of a 10% aqueous sulphuric acid continuously introduced from a feed vessel into the said stream (line 209) was sufficient to give pH=2 in the resultant mixture. The resultant mixture was separated by means of a centrifuge in the water/oil separation system (23). The organic phase was introduced at level 20 (from above) at a flow rate of 375 g/h into the distillation column (24) (30 levels, diameter 10 cm, height 5 m). The said column was operated at 150 mmHg, the temperature of the material at the bottom of the column being 70° C. and the overhead temperature being 45° C. Crude MMA was taken from the top of the column (24) at a flow rate of 288 g/h and was introduced at level 10 (from above) into the column (25) (30 levels, diameter 10 cm, height 5 m). The column (25) was operated at 250 mmHg, the temperature of the material at the bottom of the column being 80° C. and the overhead temperature being 50° C. Purified MMA was taken at a flow rate of 281 g/h from the material at the bottom of the column (25) and was introduced at level 35 (from above) into the column (26) (70 levels, diameter 10 cm, height 5 m). The column (26) was operated at 140 mmHg, the temperature of the material at the bottom of the column being 80° C. and the overhead temperature being 55° C. Pure MMA was taken from the top of the column (26) at a flow rate of 250 g/h. The total yield of methyl methacrylate isolated from methacrolein was 97.2% after the work-up described above.

TABLE 1

Summary of reactions for steps A) and B):

| Example | Reaction | Yield | Selectivity | Space-time yield, step B [mol MMA/ kg cat-h] | Overall selectivity of PA to MMA |
|---|---|---|---|---|---|
| 1 | PA-MAL | 98.1 | 98.2 | | |
| 2 | MAL-MMA | 94.8 | 96.3 | 9.3 | 94.6 |
| 3 | MAL-MMA | 83.4 | 97.5 | 14.0 | 96.0 |
| 4 | MAL-MMA | 76.5 | 97.4 | 9.8 | 95.6 |

Comparative Values from the Prior Art:

The following Comparative Examples (Comparison 5-8) collate possible processes and combinations of various processes according to the prior art with the corresponding selectivities of the individual steps and the overall processes.

COMPARATIVE EXAMPLE 5

Reaction A: Isobutylene→Methacrolein
Reaction B: Methacrolein→Methacrylic acid
Reaction C: Methacrylic acid→Methyl methacrylate
C=conversion
S=selectivity
Reaction A (e.g. U.S. Pat. No. 7,012,039B2, Example 1, Pressure <2 Bar):
S(MAL)=88.3%,
S(MAA)=2.4%
Water addition $H_2O$/MAL=1.7 (mol/mol)
Reaction B, (e.g. EP0376117B1, Example 1, pressure <2 bar)
S(MAA)=89.2%
Water addition $H_2O$/MAL=5.5 (mol/mol)
Reaction C (e.g. US20020188151A1)
S(MMA)~100%
Overall selectivity of reactions A+B+C=S(MAL+MAA from IBN)*S(MAA from MAL)*S(MMA from MAL)= 80.9%

COMPARATIVE EXAMPLE 6

Reaction A: Isobutylene Methacrolein
Reaction B: Methacrolein→Methyl methacrylate
Reaction A (e.g. U.S. Pat. No. 7,012,039B2, Example 1, Pressure <2 Bar):
S(MAL)=88.3%,
S(MAA)=2.4%
Water addition $H_2O$/MAL=1.7 (mol/mol)
Reaction B, variant 1 (U.S. Pat. No. 7,012,039B2, Example 1):
S(MMA)=90.7%
Reaction B, variant 2 (EP 2 210 664 A1, Example 7):
S(MMA)=97.2%
Overall selectivity A+B (variant 1): S(MMA from IBN)=S(MAL)*S(MMA)=80.1%
Overall selectivity A+B (variant 2): S(MMA from IBN)=S(MAL)*S(MMA)=85.8%

COMPARATIVE EXAMPLE 7

Reaction A: Propionaldehyde→Methacrolein
Reaction B: Methacrolein→Methacrylic acid
Reaction C: Methacrylic acid→Methyl methacrylate
Reaction A (e.g. DE3213681A1, Example 1)
S(MAL)=98.1%
Reaction B (e.g. EP0376117B1, Example 1, pressure <2 bar)
S(MAA)=89.2%
Water addition MAL/$H_2O$=5.5 (mol/mol)
Reaction C (e.g. US20020188151A1) S(MMA)~100%
Overall selectivity of steps A+B+C=S(MMA from PA)=S(MAL from PA)*S(MAA from MAL)*S(MMA from MAA)=87.5%

COMPARATIVE EXAMPLE 8

Reaction A: Propionaldehyde→Methacrolein
Reaction B: Methacrolein→Methyl methacrylate
Reaction A, (CN101074192A1, Pressure <2 Bar)
S(MAL)=95.2%
Reaction B, (CN101074192A1)
S(MMA)=98.2%
Overall selectivity of steps A+B: S(MMA from PA)=S(MAL)*S(MMA)=93.5%

TABLE 2

Comparison of processes (part 1)

| Comparative examples | Reaction | Overall selectivity | Extra $H_2O$ [mol/mol MMA] |
|---|---|---|---|
| 5 | IBN-MAL-MAA-MMA | 80.9 | 7.2 |
| 6 | IBN-MAL-MMA | 80.1 | 1.7 |
| | | 85.8 | |

TABLE 2-continued

Comparison of processes (part 1)

| Comparative examples | Reaction | Overall selectivity | Extra H$_2$O [mol/mol MMA] |
|---|---|---|---|
| 7 | PA-MAL-MAA-MMA | 87.5 | 5.5 |
| 8 | PA-MAL-MMA | 93.5 | — |
| 4 | PA-MAL-MMA | 95.6 | — |

Comparative processes 5 to 7 in particular require large molar amounts of separately added water during the reaction steps, while overall selectivities are markedly poorer.

TABLE 3

Comparison of processes (part 2)

| Example/ Comparative example | Reaction | Overall selectivity | Cat. for Mal synthesis [mol amine/ mol MAL] | Cat. for MMA synthesis [mol MMA/ kg cat·h] |
|---|---|---|---|---|
| 8 | PA-MAL-MMA | 93.5 | 1.040 | 3.7 |
| 4 | PA-MAL-MMA | 95.6 | 0.024 | 9.8 |

As shown in the table above, the reaction according to the invention (Example 4) can be carried out in step A) with catalytic amounts of amine base, based on MAL, while Comparative example 8 requires a stoichiometric excess of catalyst for this purpose. The value of 9.8 for the space-time yield of step B) from the claimed process is likewise more than twice as high as in Comparative example 8.

The invention claimed is:

1. A process for producing methyl methacrylate, the process comprising:
   A) producing methacrolein from propanal and formaldehyde and
   B) reacting the methacrolein in an oxidative esterification reaction to obtain methyl methacrylate,
   wherein
   the producing A) and the reacting B) take place in a liquid phase at a pressure of from 2 to 100 bar, and
   the reacting B) is carried out in the presence of a heterogeneous noble-metal-comprising catalyst comprising a metal and/or a metal oxide, and
   the reaction mixture of the producing A) is passed into a column for steam stripping, and a top phase of the steam stripper, which comprises the methacrolein and water, is then separated with a phase separator into an upper phase and a lower phase, whereby the upper phase comprises the methacrolein.

2. The process according to claim 1, wherein the producing A) is carried out in the presence of from 0.1 to 20 mol % of organic base and from 0.1 to 20 mol % of acid, based in each case on propanal.

3. The process according to claim 1, wherein the producing A) is carried out at a temperature of from 100 to 300° C.

4. The process according to claim 1, wherein the producing A) is carried out at a pressure of from 5 to 100 bar.

5. The process according to claim 1, wherein the heterogeneous oxidation catalyst comprises one or more ultrafinely dispersed metals with an average particle size of <20 nm selected from the group consisting of gold, palladium, ruthenium, rhodium, and silver.

6. The process according to claim 1, wherein the heterogeneous oxidation catalyst comprises at least one member which is in a metallic form and/or an oxidized form and which comprises a metal selected from the group consisting of lithium, sodium, potassium, calcium, magnesium, scandium, yttrium, a lanthanoid with an atomic number of from 57 to 71, silicon, titanium, zirconium, hafnium, vanadium, niobium, tantalum, chromium, molybdenum, tungsten, manganese, rhenium, iron, ruthenium, osmium, cobalt, rhodium, iridium, nickel, palladium, platinum, copper, silver, gold, zinc, cadmium, boron, aluminium, gallium, indium, thallium, germanium, tin, lead, antimony, bismuth, and tellurium.

7. The process according to claim 2, wherein the organic base comprises a secondary amine.

8. The process according to claim 2, wherein the acid comprises at least one organic acid.

9. The process according to claim 2, wherein a molar ratio of the acid to the organic base ranges from 20:1 to 1:20.

10. The process according to claim 1, wherein the producing A) is carried out with a residence time ranging from 0.1 to 300 seconds.

11. The process according to claim 1, wherein the reacting B) is carried out with a pressure ranging from 2 to 50 bar.

12. The process according to claim 1, wherein the oxidative esterification reaction is carried out at a temperature ranging from 10 to 200° C.

13. The process according to claim 1, wherein the oxidative esterification reaction takes place in the presence of methanol with a molar ratio of methanol to methacrolein ranging from 1:1 to 50:1.

14. The process according to claim 1, wherein the producing A) and the reacting B) are carried out in a continuous process.

15. The process according to claim 1, wherein a volume ratio of a reactor in the producing A) to a reactor in the reacting B) ranges from 1:1000 to 1:100.

16. The process according to claim 1, wherein a total amount of any separately added water in the producing A) and the reacting B) during the process is not greater than 100 mol %, based on methacrolein.

17. The process according to claim 1, wherein no water is separately added in the producing A) and the reacting B) during the process.

18. The process according to claim 1, wherein a content of water in reaction mixture during the reacting B) is at most 10% by weight based on a total weight of the reaction mixture.

19. The process according to claim 18, wherein no dewatering is conducted after the producing A) and before the reacting B).

* * * * *